United States Patent
Lazic et al.

(10) Patent No.: US 8,864,775 B2
(45) Date of Patent: Oct. 21, 2014

(54) APPLYING FORCEPS FOR A CLIP

(75) Inventors: Peter Lazic, Tuttlingen (DE); Daniel Lazic, Tuttlingen (DE)

(73) Assignee: Peter Lazic GmbH, Tuttlingen (DE)

( * ) Notice: Subject to any disclaimer, the term of this patent is extended or adjusted under 35 U.S.C. 154(b) by 1766 days.

(21) Appl. No.: 11/361,573

(22) Filed: Feb. 24, 2006

(65) Prior Publication Data

US 2007/0191883 A1    Aug. 16, 2007

(30) Foreign Application Priority Data

Feb. 16, 2006   (DE) .................... 20 2006 002 436 U

(51) Int. Cl.
  *A61B 17/12*   (2006.01)
  *A61B 17/122*   (2006.01)
  *A61B 17/128*   (2006.01)
  *A61B 17/10*   (2006.01)

(52) U.S. Cl.
  CPC .......... *A61B 17/1285* (2013.01); *A61B 17/1227* (2013.01); *A61B 17/10* (2013.01); *A61B 17/128* (2013.01)
  USPC ............ 606/139; 606/142; 606/151; 606/157

(58) Field of Classification Search
  USPC ......... 606/139, 148, 151, 207, 142, 157–158, 606/205, 210–211
  See application file for complete search history.

(56) References Cited

U.S. PATENT DOCUMENTS

| 3,344,649 | A | * | 10/1967 | Wood | 72/392 |
| 4,274,415 | A | * | 6/1981 | Kanamoto et al. | 606/142 |
| 4,416,266 | A | * | 11/1983 | Baucom | 606/158 |
| 4,434,795 | A | * | 3/1984 | Mericle | 606/142 |
| 4,444,187 | A | * | 4/1984 | Perlin | 606/158 |
| 4,446,865 | A | * | 5/1984 | Jewusiak | 606/142 |
| 4,932,955 | A | * | 6/1990 | Merz et al. | 606/158 |
| 5,062,846 | A | * | 11/1991 | Oh et al. | 606/158 |
| 5,304,183 | A | * | 4/1994 | Gourlay et al. | 606/142 |
| 5,368,600 | A | * | 11/1994 | Failla et al. | 606/139 |
| 5,984,934 | A | * | 11/1999 | Ashby et al. | 606/151 |
| 6,013,095 | A | * | 1/2000 | Ouchi | 606/205 |
| 6,210,418 | B1 | * | 4/2001 | Storz et al. | 606/142 |
| 6,896,684 | B2 | * | 5/2005 | Monassevitch et al. | 606/142 |

FOREIGN PATENT DOCUMENTS

DE    40 24 636 A1    2/1992
DE    40 24 638 A1    3/1992

* cited by examiner

*Primary Examiner* — Mark Mashack
(74) *Attorney, Agent, or Firm* — Hackler Daghighian & Martino

(57) ABSTRACT

An applying forceps for a clip comprises two forceps legs which can be pivoted relative to each other and comprise, on their sides facing each other or facing away from each other, each a depression or a projection for receiving a clip, wherein the depression or projection extends along an arcuate curve.

4 Claims, 3 Drawing Sheets

The applying forceps 1 for a clip shown in FIG. 1 are used for applying and removing an aneurysm clip (clamp) 20 and comprise a central or basic part 2 with a tubular shaft 3 mounted thereto, the free working end 4 of which comprises two forceps legs 5 which can be pivoted relative to each other. A slider 8 is guided in a bore 6 of the basic part 2 in such a manner that it can be axially displaced against the action of a restoring spring 7, the slider 8 being motionally coupled to an actuating mechanism (not shown in detail) of the forceps legs 5 via a guiding wire (coupling element) 9 which extends in the tubular shaft 3. Two double-armed levers 11a, 11b are disposed about different fixed axes of rotation 10a, 10b, on the basic part 2, wherein the longer lever arms 12a, 12b thereof, each being formed as handle, are disposed opposite to each other relative to the basic part 2. These longer lever arms 12a, 12b are directed towards the working end 4 of the tubular shaft 3. The crossing shorter lever arms 13a, 13b of the two double-armed levers 11a, 11b are hinged to the slider 8 via a connecting arm 14a, 14b each. The two axes of rotation 10a, 10b are offset relative to the central axis of the basic part 2 to permit central passage of the guiding wire 9 through the basic part 2. In the embodiment shown, the restoring spring 7 is a helical or spiral spring which is disposed in the bore 6 and is supported on the one hand on the slider 8 and on the other hand on an adjusting screw 15 screwed into the bore 6. The force of the restoring spring 7 can be adjusted through turning the adjusting screw 15. The bore 6 and the slider 8 have a non-circular, e.g. rectangular, cross-section which secures, i.e. stabilizes, the slider 8 and the two double-armed levers 11a, 11b in the basic part 2 against rotation.

APPLYING FORCEPS FOR A CLIP

CROSS REFERENCE TO RELATED APPLICATIONS

This application claims priority under 35 U.S.C. §119(a) to German Utility Model Application No. 20 2006 002 436.0, filed Feb. 16, 2006, the entire contents of which are hereby incorporated by reference.

TECHNICAL FIELD

This application relates to an applying forceps for a clip, in particular, an applying forceps for an aneurysm clip, comprising two forceps legs which can be pivoted relative to each other and are designed to receive a clip (clamp).

BACKGROUND

Forceps for application of a clip of this type are disclosed e.g. in DE 40 24 636 A1 or DE 40 24 638 A1.

The forceps for application of a clip disclosed in DE 40 24 636A 1and DE 40 24 638 A1comprise two claws at their working ends for gripping a clip, the claws being pivotable relative to each other. However, the clip can be gripped only in one single angular position, i.e. when the forceps for application of a clip is positioned in the longitudinal direction of the clip which is sometimes impossible or very difficult during use, i.e. during application and removal of the clip.

It is the object of the present invention to solve this problem.

SUMMARY

This object is achieved in accordance with the invention with an applying forceps for a clip comprising two forceps legs which can be pivoted relative to each other and comprise, on their sides facing each other or facing away from each other, each a depression or a projection for receiving a clip, wherein the depression or projection extends along an arcuate curve. The depression or projection preferably extends along an outwardly arcuated curve and through at least approximately 180°, preferably at least approximately 270°.

The advantage of the inventive applying forceps for a clip consists in that the clip can be gripped, applied and deposited by the applying forceps for a clip at any angular position along the arcuate depressions or projections. The curvature and geometry of the depressions or projections are selected in correspondence with the geometry of the clips to be used in such a manner that the clip safely engages in or on the depressions or projections at any possible angular position.

The depression or projection preferably extends along a circular or oval curve, i.e. along a curve without corners.

In preferred embodiments, the forceps legs are widened in the region of the curve, in particular, like a plate.

Further advantages of the invention can be extracted from the description and the drawing. The features mentioned above and below may be used individually or collectively in arbitrary combination. The embodiments shown and described are not to be understood as exhaustive enumeration but have exemplary character for describing the invention.

DETAILED DESCRIPTION

Figure 1:
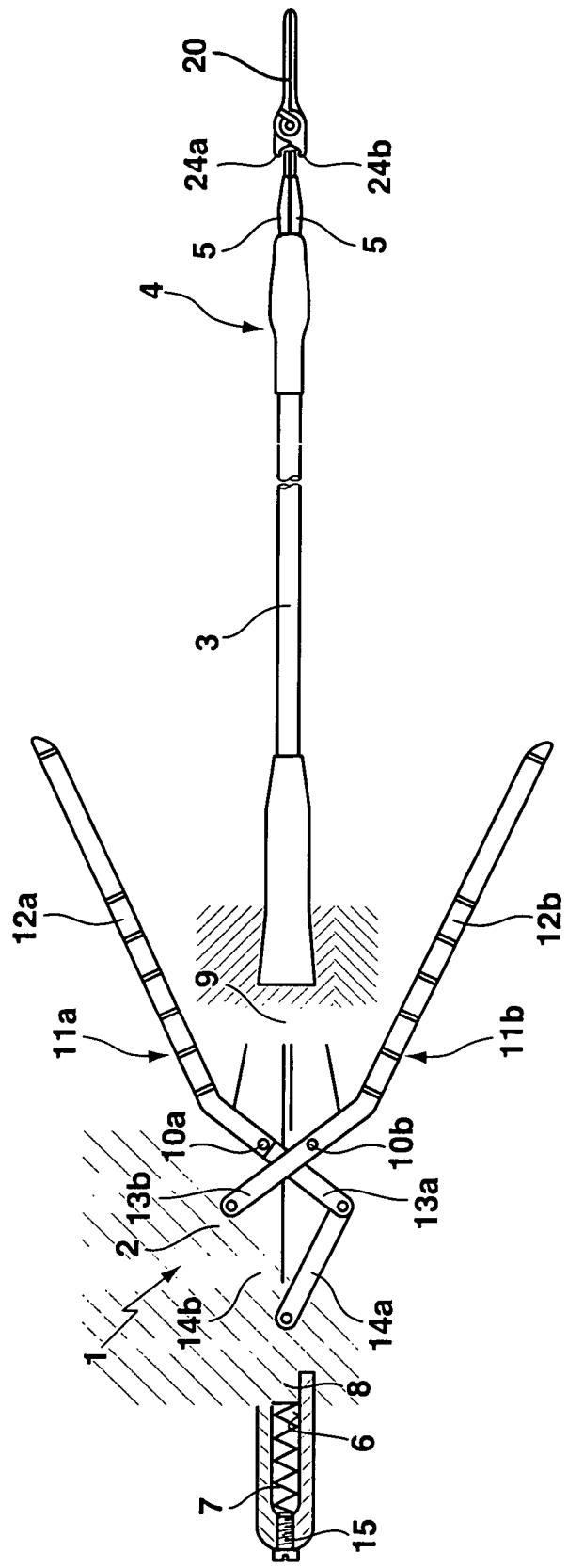
FIG. 1 shows the inventive applying forceps for a clip, partially in sectional view, with the forceps legs being closed, ready for gripping a closed aneurysm clip.
Figure 2:
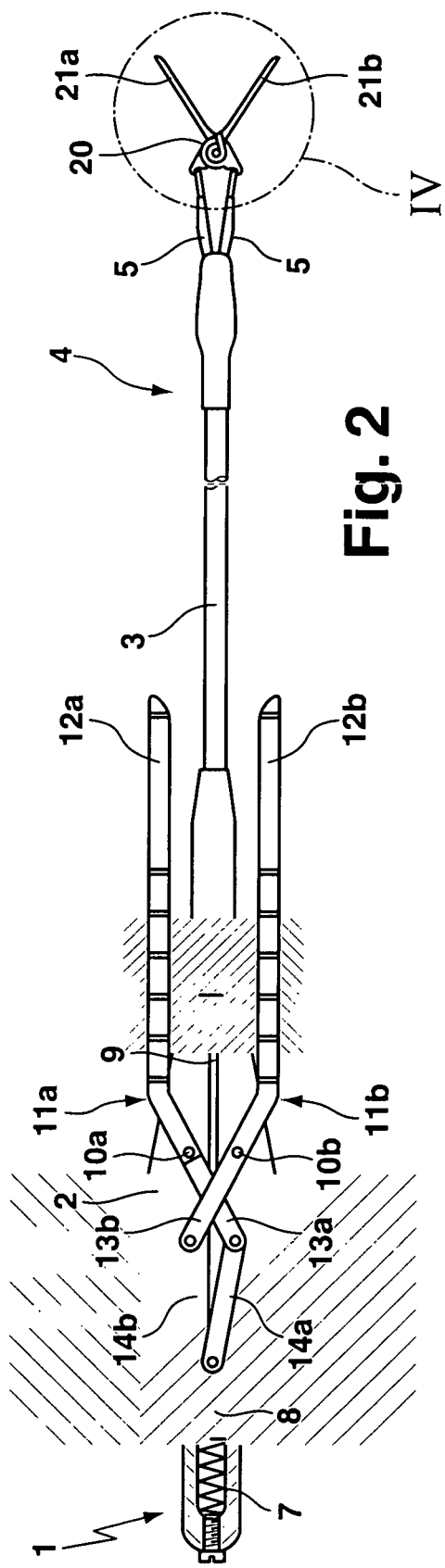
FIG. 2 shows the applying forceps for a clip of FIG. 1, wherein the forceps legs are open for gripping the aneurysm clip, thereby opening it.

In the initial position of the applying forceps 1 for a clip shown in FIG. 1, the longer lever arms 12a, 12b protrude to the outside. When the user compresses the longer lever arms 12a, 12b, the slider 8 is pushed away from the working end 4, i.e. to the left hand side in FIG. 1, via the connecting arms 14a, 14b against the action of the restoring spring 7. This motion of the slider 8 is transferred via the guiding wire 9 to the actuating mechanism which opens the forceps legs 5, which thereby grip the aneurysm clip 20 and open it. This working position of the applying forceps 1 for a clip is shown in FIG. 2. When the compressive force on the longer lever arms 12a, 12b is released, the restoring spring 7 pushes the slider 8 to the right hand side and thereby also pushes the double-armed levers 11a, 11b and the forceps legs 5 into their initial positions as shown in FIG. 1. The double-armed levers 11a, 11b causes a force ratio so that less force is required to compress the double-armed levers 11a, 11b against the action of the restoring spring 7, or the restoring spring 7 may be correspondingly more powerful.

Figure 3:
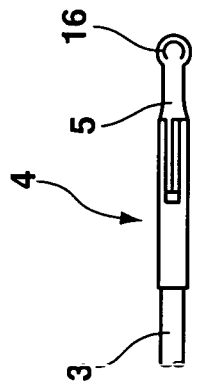
FIG. 3 shows a side view of one of the forceps legs of FIG. 1.

As is shown in FIG. 3, the free ends of the two forceps legs 5 gripping the aneurysm clip 20 are widened in the form of a plate and have a circular depression 16 in the form of an annular groove on their outer sides facing away from each other, for gripping the aneurysm clip 20. In the embodiment shown, the circular depression 16 has the shape of a partial circle extending through approximately 270° about an axis 18 which is defined by the two center points of the two circular depressions 16. Instead of an annular groove the depression 16 can also be formed by a circular hole.

Figure 4:
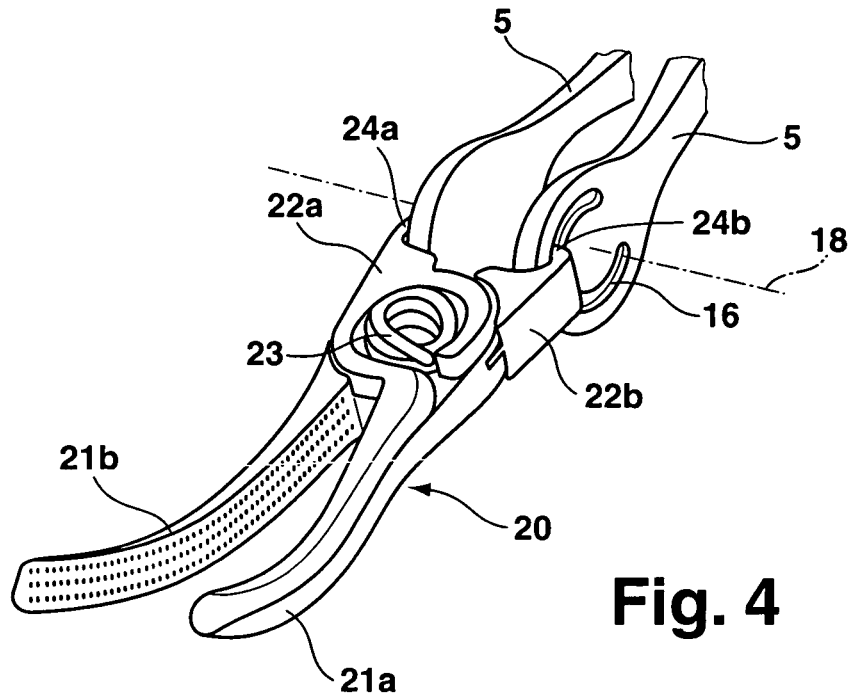
FIG. 4 shows a perspective detailed view of the forceps legs gripping the aneurysm clip in accordance with IV of FIG. 2.

As is shown in FIG. 4, the aneurysm clip 20 consists of two crossing forceps-like arms each comprising one mouth piece 21a, 21b and one operational end 22a, 22b, and being connected to each other via a pivot joint. The pivot joint is formed by a helical spring 23 formed as bearing bushing which biases the two mouth pieces 21a, 21b into the closed position shown in FIG. 1. The free ends of the operational ends 22a, 22b comprise inwardly directed projections 24a, 24b, for moving apart the mouth pieces 21a, 21b through forcing the operational ends 22a, 22b. In order to grip the aneurysm clip 20, the user positions the applying forceps 1 for a clip such that its forceps legs 5 are between the two operational ends 22a, 22b, and opens the forceps legs 5, whereby the projections 24a, 24b of the aneurysm clip 20 engage in the depression 16 and the aneurysm clip 20 is opened.

Due to the circular depression 16, the aneurysm clip 20 can be gripped by the applying forceps 1 for a clip at any angular position relative to the axis 18. The radius and the geometry of the circular depression 16 are selected in correspondence with the geometry of the projections 24a, 24b of the aneurysm clip 20 in such a manner that the projections 24a, 24b of the aneurysm clip 20 safely engage in the circular depressions 16 of the applying forceps 1 for a clip at any possible angular position thereof.

Figure 5A:
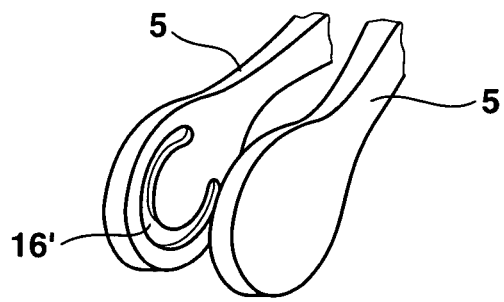
FIGS. 5a through 5c show modified forceps legs in a view analog to FIG. 4.
Figure 5B:
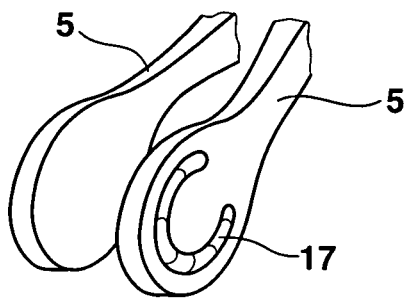
Figure 5C:
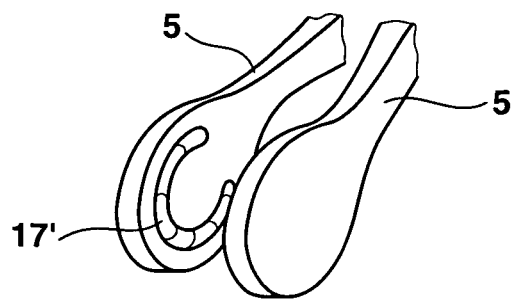

Concerning aneurysm clips whose projections on the operational ends face to the outside, the free ends of the two forceps legs 5 gripping the aneurysm clip have each one circular depression 16" on their mutually facing inner sides (FIG. 5a). Concerning aneurysm clips with operational ends having grooves or notches instead of projections, the free ends of the two forceps legs 5 gripping the aneurysm clip have each one circular projection 17 (FIG. 5b) on their outer sides facing away from each other, or one circular projection 17" (FIG. 5c) on their mutually facing inner sides.

What is claimed is:

1. Arrangement comprising:
   an applying forceps for gripping a clip, the forceps comprising two pivotable forceps legs having plate-shaped free ends, each plate-shaped free end having an inner side and an outer side, the inner sides of the plate-shaped free ends facing each other and the outer sides of the plate-shaped free ends facing away from each other in a closed position of the forceps, each of the outer sides having a depression for gripping a clip at different angular positions, wherein the depressions are each formed by an annular groove for gripping a clip at any angular position along the groove and, in the closed position of the forceps, the centers of the partial-circular grooves define an axis about which the annular grooves extend; and
   a clip comprising of two crossing forceps-like arms each arm comprising one mouth piece and one operational end connected to each other via a pivot joint, a free end of each operational end comprising projections for engagement with the annular grooves of the applying forceps at any possible angular position in order to open the mouth pieces of the clip.

2. Arrangement according to claim 1, wherein the annular grooves extends through at least approximately 180°.

3. Arrangement for a clip according to claim 2, wherein the annular grooves extends through at least approximately 270°.

4. Arrangement according to claim 1, wherein the annular grooves are mirror symmetrical relative to a longitudinal central plane of the applying forceps for a clip.

\* \* \* \* \*